United States Patent
Taniguchi et al.

(10) Patent No.: US 11,273,136 B2
(45) Date of Patent: Mar. 15, 2022

(54) METHOD FOR INCREASING PROTEIN CONTENT IN MILK OF LACTATING COWS

(71) Applicant: neopharma Japan Co., Ltd., Tokyo (JP)

(72) Inventors: Shin Taniguchi, Tokyo (JP); Yoko Noguchi, Tokyo (JP); Kan Sato, Tokyo (JP)

(73) Assignee: neopharma Japan Co. LTD., Tokyo (JP)

( * ) Notice: Subject to any disclaimer, the term of this patent is extended or adjusted under 35 U.S.C. 154(b) by 51 days.

(21) Appl. No.: 16/789,780

(22) Filed: Feb. 13, 2020

(65) Prior Publication Data

US 2020/0297676 A1 Sep. 24, 2020

(30) Foreign Application Priority Data

Feb. 15, 2019 (JP) .............................. JP2019-025275

(51) Int. Cl.
*A61K 31/197* (2006.01)
*A61K 9/00* (2006.01)

(52) U.S. Cl.
CPC .......... *A61K 31/197* (2013.01); *A61K 9/0053* (2013.01)

(58) Field of Classification Search
CPC ............................ A61K 31/197; A61K 9/0053
See application file for complete search history.

(56) References Cited

U.S. PATENT DOCUMENTS

| | | | |
|---|---|---|---|
| 5,871,773 A | 2/1999 | Rode et al. | |
| 2013/0316031 A1 | 11/2013 | Kaneda et al. | |

FOREIGN PATENT DOCUMENTS

| | | |
|---|---|---|
| JP | S60259148 A | 12/1985 |
| JP | H06153816 A | 6/1994 |
| JP | H06237701 A | 8/1994 |
| WO | 2012/093533 A1 | 7/2012 |

OTHER PUBLICATIONS

Hyeong-Rak et al. (KR 2003-0097164, See English translation) (Year: 2003).*
The Cattle Site (https://www.thecattlesite.com/articles/4248/managing-cow-lactation-cycles/, May 18, 2015). (Year: 2015).*
Lee et al., Indian J of Animal Sciences 86 (7), 781-785, Jul. 2016. (Year: 2016).*
Trends in Milk Consumption. Agriculture & Livestock Industries Corporation, Planning and Coordination Department. https://www.alic.go.jp/koho/kikaku03_000743.html. Jul. 2014.
Aoki et al., Time Course of Changes in Antioxidant Activity of Milk From Dairy Cows Fed a Trehalose-Supplemented Diet. Animal Science Journal (2013) 84, pp. 42-47.
Slyter. Influence of Acidosis on Rumen Function. Feed Energy Conservation Laboratory, Animal Physiology and Genetics Institute Beltsville Agriculture Research Center. JOurnal of Animal Science 43(4) 1976, pp. 910-929.
Website Program of the 124th Annual Meeting of Japanese Society of Animal Science. <http://jsas124.org/> Feb. 2018. pp 1-4.
The Effects of 5-Aminolevulinic Acid Supplementation on Rumen Fermentation and Performance of Dairy Cows. Japanese Society of Animal Science. Mar. 2018, 4pgs.
Hendawy. Effects of 5-Aminolevulinic Acid (5-ALA) Supplementation on Immune Response and Performance of Dairy Cows. Mar. 2018, pp. 1-35.

* cited by examiner

*Primary Examiner* — Umamaheswari Ramachandran
(74) *Attorney, Agent, or Firm* — Occhiuti & Rohlicek LLP

(57) ABSTRACT

An object of the present invention is to increase a protein content in milk of a lactating cow. When 5-ALA, an amino acid, or ALAs which are derivatives thereof or salts thereof, are mixed with a feed and administered to a lactating cow without being treated such as coating, a lactation yield remained substantially unchanged but the obtained milk had significantly high proportion (%) of proteins, particularly casein, when compared with milk collected from milk cows who had consumed a conventional feed.

2 Claims, No Drawings

METHOD FOR INCREASING PROTEIN CONTENT IN MILK OF LACTATING COWS

TECHNICAL FIELD

The present invention relates to a method for increasing a protein content in milk of a lactating cow, and more particularly relates to a method for increasing a protein content in a lactating cow, comprising 5-aminolevulinic acid (5-ALA) or derivatives thereof, or salts thereof (hereinafter also referred to as "ALAS").

Cow's milk consumption in Japan increased steadily from 2,010,000 kiloliters in 1966 to 5,050,000 kiloliters in 1996 with population growth and westernization of food (for example, see Non-patent Document 1). However, the consumption of cow's milk has been declining slightly in recent years because of a falling birthrate and an aging population and the diversified beverage market, and the dairy industry has been continuously making efforts to provide high-quality cow's milk and value-added dairy products at low costs to maintain consumption.

For the production of quality improved cow's milk, proposals have been made on a feed composition for the milking cow comprising 30 to 60 parts by weight of an n-3 fatty acid supply source, 7 to 20 parts by weight of a carbohydrate supply source, 3 to 6 parts by weight of powdery dry grass, 30 to 50 parts by weight of a coemulsifier, and 0.05 to 0.15 parts by weight of an antioxidant (for example, see Patent Document 1), an agent for improving milk yield and/or milk quality in a ruminant comprising a cashew nut shell liquid, anacardic acid, cardanol and/or cardol (for example, see Patent Document 2), and a feed supplement for lactating dairy cows comprising a basic cereal grain mixture having a proportion of proteins of at least approximately 12% by weight, approximately 2 to 12% by weight (of the weight of this supplement) of an essentially saturated fat which is added, and approximately 0.5 to 4.5% by weight (of the weight of this supplement) of a non-protein source of nitrogen (for example, see Patent Document 3).

On the other hand, in ruminants such as cows and sheep, proteins and amino acids consumed are known to be rapidly decomposed to ammonia and carbon dioxide gas by microorganisms in the rumen (for example, see Non-patent Documents 2 and 3), and it is thus considered to be extremely difficult for ruminants to efficiently utilize all the proteins and amino acids comprised in a feed. For this reason, proposed is a method for increasing milk production in a ruminant comprising feeding a feed additive comprising lysine and methionine, as essential components, protected from the action of microorganisms in the rumen of the ruminant by coating beginning between 60 days prior to the scheduled parturition date of the ruminant and 29 days after the parturition and continuing the feeding until any day between day 30 and day 150 of a milk production period (for example, see Patent Document 4).

PRIOR ART DOCUMENTS

Patent Documents

[Patent Document 1] Japanese unexamined Patent Application Publication No. 06-153816
[Patent Document 2] International Publication No. WO2012/093533
[Patent Document 3] Japanese unexamined Patent Application Publication No. 60-259148
[Patent Document 4] Japanese unexamined Patent Application Publication No. 6-237702

Non-Patent Documents

[Non-patent Document 1] Agriculture & Livestock Industries Corporation website (https://www.alic.go.jp/koho/kikaku03_000743.html)
[Non-patent Document 2] Animal Science Journal, 84(1), 42-47, 2013
[Non-patent Document 3] Journal of Animal Science, 43(4), 910-929, 1976

SUMMARY OF THE INVENTION

Object to be Solved by the Invention

An object of the present invention is to increase a protein content in milk of a lactating cow.

Means to Solve the Object

The present inventors have studied various feeds and feed additives to increase a protein content in milk of a lactating cow and found that when 5-ALA, an amino acid, or ALAs which are derivatives thereof or salts thereof, are mixed with a feed and administered to a lactating cow without being treated such as coating, a lactation yield remained substantially unchanged and there was no significant difference in milk fat content, lactose, total solid or non-fat solid in the collected milk from the milk collected from milk cow groups who had consumed a conventional feed. However, it was unexpectedly confirmed that proteins, particularly casein, in the collected milk were comprised in a significantly larger proportion (%) than in the milk collected from milk cow groups who had consumed a conventional feed, whereby the present invention has been accomplished.

More specifically, the present invention is as follows.
[1] A method for increasing a protein content in milk of a lactating cow, comprising orally administering a compound shown by the following formula (I) or salt thereof to the lactating cow in an amount of 0.200 to 2 mg/kg of body weight/day in terms of 5-aminolevulinic acid.

[Formula 1]

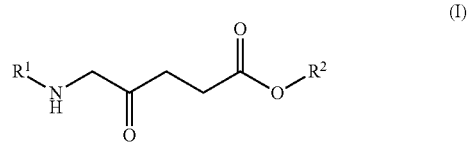

(I)

(wherein $R^1$ represents a hydrogen atom or an acyl group, $R^2$ represents a hydrogen atom, a linear or branched alkyl group, a cycloalkyl group, a cycloalkenyl group, an aryl group or an aralkyl group).
[2] The method for increasing a protein content in milk of a lactating cow according to the above [1], wherein the protein is casein.
[3] A method for producing cow's milk having an increased protein content, comprising using the method according to the above [1] or [2].

Other embodiments of the present invention include an agent for increasing a protein content in milk of a lactating cow comprising the compound shown by the above formula (I) or salt thereof, a feed to which the agent for increasing a protein content is added, the compound shown by the formula (I) or salt thereof to be used as the agent for increasing a protein content to increase a protein proportion in milk of a lactating cow, use of the compound shown by the formula (I) or salt thereof for the preparation of the agent for increasing a protein content in milk of a lactating cow, and use of the compound shown by the formula (I) or salt thereof for the preparation of a feed for ruminants such as a cow for increasing a protein content in milk of a lactating cow.

Effect of the Invention

When ALAs, or the agent for increasing a protein content in milk of a lactating cow comprising ALAs, of the present invention is orally administered to the lactating cow, a content of proteins, of which casein, in lactated milk can be increased in cows, in which amino acids consumed are known to be decomposed by microorganisms present in the rumen. Additionally, when ALAs, or a feed to which the agent for increasing a protein content comprising ALAs is added, is administered to a lactating cow, cow's milk having an increased protein content can be produced.

MODE OF CARRYING OUT THE INVENTION

The method for increasing a protein content in milk of a lactating cow of the present invention is not particularly limited as long as a method comprises orally administering a compound shown by the above formula (I) or salt thereof to the lactating cow in an amount of 0.200 to 2 mg/kg of body weight/day in terms of 5-aminolevulinic acid, and the agent for increasing a protein content in milk of a lactating cow of the present invention is not particularly limited as long as it is an agent for increasing a protein content in milk of a lactating cow comprising the compound shown by the above formula (I) or salt thereof, and such ALAs and the agent for increasing a protein content can be used together with other agents for increasing a protein content in milk of lactating cow, beans, grains, lipids, non-protein nitrogen sources, various vitamins such as vitamin A, vitamin B1, B2, B6, B12, vitamin C, vitamin D, and vitamin E, and the like.

In the present invention, the milk of a lactating cow is not particularly limited as long as it is a liquid secreted from mammary glands when a lactogenic hormone acts on mammary glands after a female cow delivered and includes so-called normal milk used for producing daily products such as cow's milk, cheese, and yogurt consumed by human or the like, without necessarily including colostrum having very high nutritious value and comprising vital components to immunize a calf and produced for 5 to 6 days after delivery.

In the present invention, proteins are building components of life forms comprised in the above milk and polymer compounds in which amino acids are linked via peptide bonds (amino-carbonyl bond) like a chain, and can be roughly categorized into casein which deposits and solidifies when pH decreases to 4.6; and whey protein comprising a mixture of spherical proteins such as α-lactalbumin, β-lactoglobulin, immunoglobulin, whey albumin, and lactoferrin produced as remaining components when casein solidifies.

In the present invention, the method for measuring a (total) protein content in milk of a lactating cow is not particularly limited as long as it is a known measurement method, and examples include the Kjeldahl method in which a solution wherein a test sample is thermally decomposed under a strong acid and subsequently alkalized by adding strong alkali is steam-distilled, and produced ammonia is quantitatively determined to calculate an amount of nitrogen, the Dumas method in which a sample is combusted and reduced at a high temperature and an amount of nitrogen is quantitatively determined from the produced nitrogen gas, a measurement method using an ultraviolet and visible spectrophotometer by utilizing the nature of amino acids having an aromatic group absorbing UV light at about 280 nm, the Bradford method utilizing an electrostatic interaction between basic amino acid residues and terminal amino acids in a sample and a triphenylmethane pigment Coomassie Brilliant Blue, the Biuret method utilizing the nature that when tripeptide or higher oligopeptides in a sample or nitrogen atoms in proteins form coordinate bonds with Cu(II), the color of solution develops a red-purple color, and Lowry method and BCA method which are modified Biuret methods.

Additionally included is a fluorescence method which detects fluorescence emitted by for example, fluorescamine which reacts with primary amines in proteins in a sample; o-phthalaldehyde (OPA) which reacts with primary amines in proteins in a sample in the presence of a reducing agent such as 2-mercaptoethanol; and 3-(4-carboxybenzoyl)quinoline-2-carbox-aldehyde (CBQCA) which reacts with primary amines in proteins in a sample in the presence of cyanide ions; and also included is a method of protein quantitative determination using polyacrylamide gel electrophoresis.

In the present invention, a case where a protein content is increased in milk of a lactating cow refers to a case where a protein proportion in the composition of milk collected from a lactating cow to which ALAs, or the agent for increasing a protein content comprising ALAs, is administered is higher by 0.01% or more, preferably 0.02% or more, preferably 0.03% or more, and more preferably 0.04% or more, than a protein proportion in the milk composition of a test milk collected from a lactating cow to which ALAs, or the agent for increasing a protein content comprising ALAs, is not administered.

Examples of the casein described above include a phosphoprotein which accounts for about 80% of all proteins in cow's milk and deposits at 20° C. when pH is adjusted to 4.6, wherein an amino acid (serine) and phosphoric acid are bound. Casein can be further categorized into α-casein, β-casein, and κ-casein, and α-casein can be further categorized into αS1-casein and αS2-casein, however, in milk the individual casein does not behave singly in separation but suspend as gigantic colloidal particles while interacting with each other.

In the present invention, the method for measuring a content of casein in milk of a lactating cow includes a method in which an acid is added to a test milk sample to adjust pH to 4.6 or lower and a deposited casein sample is prepared, to which any of the above methods for measuring a protein content is applied to calculate a content of casein in the test milk sample, but a content of casein can also be analyzed using a commercial automatic analyzer which can analyze the composition of a milk sample together with other items such as proteins, lactose, non-fat solid, overall solid, MUN, and somatic cell count.

In the present invention, a case where casein is increased in milk of a lactating cow refers to a case where a casein proportion in the milk composition of milk collected from a lactating cow to which ALAs, or the agent for increasing a protein content comprising ALAs, is administered, is higher by 0.005% or more, preferably 0.01% or more, and preferably 0.02% or more, than a casein proportion in the milk composition of a test milk collected from a lactating cow to which ALAs, or the agent for increasing a protein content comprising ALAs, is not administered.

The applicable subject for the agent for increasing a protein content of the present invention is not particularly limited as long as it is a domesticated or wild cow belonging to the genus *Bos*, subfamily Bovinae, and examples of the domesticated cow include a beef cow, a milk cow, a milk and beef cow, and a working cow, and specific examples thereof include beef cows such as Aberdeen Angus species, Hereford species, Shorthorn species, Charolais species, Limousin species, Japanese Black species, Japanese Brown species, Japanese Shorthorn species, and Japanese Polled species; milk cows such as Brown Swiss species, Guernsey species, Holstein species, Jersey species, Kelly species, Milking Devon species, and Norwegian Red species; and crossbred cows thereof, and milk cows such as Brown Swiss species, Guernsey species, Holstein species, Jersey species, Kelly species, Milking Devon species, and Norwegian Red species are preferable. Additionally, the lactating cow in the present invention is not particularly limited as long as it is a cow who has reached a reproductive age and is lactating, and examples include a cow whose protein content proportion in milk needs to be increased. In the present invention, the lactating cow can encompass, for convenience, a pre-lactating cow who is not yet lactating in reality but expected to deliver and needs to increase a protein content in milk during a lactation period.

Preferable examples of the above ALAs include 5-ALA wherein $R^1$ and $R^2$ in the formula (I) each represent a hydrogen atom or salt thereof. 5-ALA is an amino acid also called 5-aminolevulinic acid. Additionally, examples of the 5-ALA derivative include compounds other than 5-ALA wherein $R^1$ in the formula (I) represents a hydrogen atom or an acyl group, and $R^2$ in the formula (I) represents a hydrogen atom, a linear or branched alkyl group, a cycloalkyl group, a cycloalkenyl group, an aryl group or an aralkyl group.

Examples of the acyl group in the formula (I) include linear or branched alkanoyl groups having 1 to 8 carbon atoms such as a formyl group, an acetyl group, a propionyl group, a butyryl group, an isobutyryl group, a valeryl group, an isovaleryl group, a pivaloyl group, a hexanoyl group, an octanoyl group, and a benzylcarbonyl group, and aroyl groups having 7 to 14 carbon atoms such as a benzoyl group, a 1-naphthoyl group, and a 2-naphthoyl group.

Examples of the alkyl group in the formula (I) include linear or branched alkyl groups having 1 to 8 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a heptyl group, and an octyl group.

Examples of the cycloalkyl group in the formula (I) include cycloalkyl groups having 3 to 12 carbon atoms such as a cyclopropyl group, a cyclobutyl group, a cyclopentyl group, a cyclohexyl group, a cycloheptyl group, a cyclooctyl group, a cyclodecyl group, and a cyclododecyl group.

Examples of the cycloalkenyl group in the formula (I) include cycloalkenyl groups having 3 to 12 carbon atoms such as a cyclopropenyl (for example, 1-cyclopropenyl) group, a cyclobutenyl (for example, 1-cyclobutenyl) group, a cyclopentenyl (for example, 1-cyclopentenyl) group, a cyclohexenyl (for example, 1-cyclohexenyl) group, a cycloheptenyl (for example, 1-cycloheptenyl) group, a cyclooctenyl (for example, 1-cyclooctenyl) group, a cyclodecenyl (for example, 1-cyclodecenyl) group, and a cyclododecenyl (for example, 1-cyclododecenyl) group.

Examples of the aryl group in the formula (I) include aryl groups having 6 to 18 carbon atoms such as a phenyl group, a naphthyl (for example, 1-naphthyl) group, an anthryl (for example, 1-anthryl) group, a phenanthryl (for example, 1-phenanthryl) group, and a pyrenyl (for example, 1-pyrenyl) group.

Examples of the aralkyl group in the formula (I) include the same examples as the above aryl group for the aryl moiety and the same examples as the above alkyl group for the alkyl moiety, and specifically include aralkyl groups having 7 to 15 carbon atoms such as a benzyl group, a phenethyl group, a phenylpropyl group, a phenylbutyl group, a benzhydryl group, a trityl group, a naphthylmethyl group, and a naphthylethyl group.

The above ALA derivative is preferably a compound wherein $R^1$ represents a formyl group, an acetyl group, a propionyl group, a butyryl group, or the like, and a compound wherein the above $R^2$ represents a methyl group, an ethyl group, a propyl group, a butyl group, a pentyl group, or the like, and preferable examples of the above $R^1$ and $R^2$ combination include combinations of a formyl group and a methyl group, an acetyl group and a methyl group, a propionyl group and a methyl group, a butyryl group and a methyl group, a formyl group and an ethyl group, an acetyl group and an ethyl group, a propionyl group and an ethyl group, and a butyryl group and an ethyl group.

ALAs only need to work as the active component in vivo in the form of 5-ALA of the formula (I) or a derivative thereof, and can be administered, depending on the dosage form, in the form of various salts to raise the solubility or in the form (for example, an ester) of a prodrug (precursor) which is metabolized by enzymes in vivo and then acts to improve intestinal absorbability, tissue migration properties, tissue selectivity, chemical stability, and the like, or reduce side effects. Examples of the 5-ALA and salt of derivative thereof include a pharmacologically acceptable acid-addition salt, a metal salt, an ammonium salt, and an organic amine-addition salt. Examples of the acid-addition salt include inorganic acid salts such as a hydrochloric acid salt, a hydrobromic acid salt, a hydriodic acid salt, a phosphoric acid salt, a nitric acid salt, and a sulfuric acid salt, and organic acid-addition salts such as a formic acid salt, an acetic acid salt, a propionic acid salt, a toluene sulfonic acid salt, a succinic acid salt, an oxalic acid salt, a lactic acid salt, a tartaric acid salt, a glycolic acid salt, a methanesulfonic acid salt, a butyric acid salt, a valeric acid salt, a citric acid salt, a fumaric acid salt, a maleic acid salt, and a malic acid salt. Examples of the metal salt include alkali metal salts such as a lithium salt, a sodium salt, and a potassium salt, alkaline earth metal salts such as a magnesium and a calcium salt, and metal salts such as aluminum and zinc. Examples of the ammonium salt include alkyl ammonium salts such as an ammonium salt, and a tetramethyl ammonium salt. Examples of the organic amine salt include various salts such as a triethylamine salt, a piperidine salt, a morpholine salt, and a toluidine salt. These salts can also be used as a solution when used.

Of the above ALAs, desirable is 5-ALA and various esters such as a 5-ALA methyl ester, a 5-ALA ethyl ester, a 5-ALA propyl ester, a 5-ALA butyl ester, and a 5-ALA pentyl ester, and a hydrochloric acid salt, a phosphoric acid salt, and a sulfuric acid salt thereof, with a 5-ALA hydrochloric acid salt and a 5-ALA phosphoric acid salt being particularly preferable examples.

The above ALAs can be produced by any of the known methods such as chemical synthesis, production by microorganism or production by enzymes. Additionally, the above ALAs may form a hydrate or a solvate, or any of these can be used singly or 2 or more can be used in a suitable combination.

For the form of use, ALAs, or the agent for increasing a protein content comprising ALAs, can be prepared as a granule form, a grain form, a powder form, or a solution form and administered by being added to a feed usually given to a cow, and can also be used in the form of an oral administration preparation such as a powder, a granule, a fine granule, and a tablet; or an injection preparation such as a liquid and a powder to be dissolved before use. Administration method of the above preparations include oral administration, intravenous administration, intramuscular administration, local administration, intraperitoneal administration, dermal administration, and transrectal administration.

The dose of ALAs, or the agent for increasing a protein content comprising ALAs, when orally administered to a lactating cow, is not particularly limited as long as the effect of the present invention is provided and examples include, per kg of body weight of a cow, in term of aminolevulinic acid, 0.02 to 2 mg/day, preferably 0.05 to 1 mg/day, more preferably 0.075 to 0.75 mg/day, further preferably 0.1 to 0.6 mg/day, and particularly preferably 0.2 to 0.4 mg/day.

A method for feeding a feed when ALAs, or the agent for increasing a protein content comprising ALAs, is used by being added to the feed includes feed supplying methods such as a separate feeding method in which feeding is carried out 2 to 4 times a day and an ad libitum feeding in which a cow is allowed to consume feed at any time without setting specific food giving time. The feed to which ALAs are added is not particularly limited as long as it is a feed generally used for supplying with a cow, and feeds prepared from conventionally known feed materials such as corn, soybean meal, alfalfa, chaff, wheat bran, rice bran, alfalfa, oat hay, cottonseed oil meal, bone meal, lime, dicalcium phosphate, sodium chloride, urea, and molasses can be used, and a commercial feed for cows can be used.

The feeding period of a feed when ALAs, or the agent for increasing a protein content comprising ALAs, is used by being added to the feed is not particularly limited as long as the effect of the present invention is provided and examples include 1 day to 3 months, preferably 3 days to 2 months, more preferably 1 week to 1 month, further preferably 10 days to 20 days, and particularly preferably 12 days to 16 days.

Hereinafter, the present invention is specifically described with reference to examples but the technical scope of the present invention is in no way limited thereto.

EXAMPLE

The following test was carried out with the approval of Tokyo University of Agriculture and Technology, the Laboratory Animal Subcommittee.

Effects of ALAs on the milk composition of a lactating cow was studied. Six lactating Holstein milk cows (average body weight 698±18 kg, average milk production 24.1±1.6 kg/d, average days-in-milk (DIM) 209±34 days, and average number of lactations 2.9±0.4) were placed in a free stable. After a 7-day grace period, 6 cows were randomly assigned to section A and section B (each group n=3). Section A had, after a grace period, an ALA administration period of 14 days (ALA Consumption Group A), with an adjustment period of 7 days interposed, followed by an ALA non-administration period of 14 days (Control Group A), whereas Section B had, after a grace period, an ALA non-administration period of 14 days (Control Group B), with an adjustment period of 7 days interposed, followed by an ALA administration period of 14 days (ALA Consumption Group B), whereby the test was carried out by the crossover method. The details are as shown in the following Table 1. A total mixed ration (TMR) (see Table 2) which had been used was fed during the above grace period, adjustment period and ALA non-administration period, and a feed to which 10 mg of 5-ALA was added per kg of the total mixed ration (TMR) was fed during the ALA administration period.

TABLE 1

|  | 7 Days | 14 Days | 7 Days | 14 Days |
| --- | --- | --- | --- | --- |
| Section A | Grace period | ALA administration period (ALA Consumption Group A) | Adjustment period | Non-administration period (Control Group A) |
| Section B | Grace period | Non-administration period (Control Group B) | Adjustment period | ALA administration period (ALA Consumption Group B) |

5-ALA was provided by neopharma Japan Co., Ltd. Each feed and water were available at any time but feed consumption of each group on a dry base was 23.4 kg/day per cow in the control groups and 23.6 kg/day per cow in the ALA groups. Thus, the daily consumption of 5-ALA in the ALA groups was 0.329.6 mg to 0.347.1 mg/kg b.w./day. Each of the milk cows was milked at 09:00 and 17:00 and allowed to consume each feed at any time after milking.

TABLE 2

| Composition | % (Dry mass) |
| --- | --- |
| Materials | |
| Corn silage | 34 |
| Sudangrass hay | 9.6 |
| Alfalfa hay cube | 11.2 |
| Concentrated components*[1] | 20.8 |
| Wheat bran | 11.2 |
| Soybean meal | 7.6 |
| Rice bran | 5.7 |
| Nutrient components*[2] | |
| Digestible nutrients | 72.7 |
| Crude proteins | 16.9 |
| Ether extract | 3.7 |
| Neutral detergent fiber | 36.9 |

*[1]47% grains (corn, barley, wheat flour, milo, ley), 27% chaff•bran (rice bran, corn gluten feed, wheat bran), 22% oilseed meal (soybean meal, rapeseed meal, corn gluten meal, flaxseed meal), 4% other materials (molasses, calcium, carbonate, sodium chloride, phosphate)
*[2]Estimated from Standard Tables of Feed Composition in Japan (Ministry of Agriculture, Forestry and Fisheries, Commission of Inquiry Secretariat)

(Milk Sample Collection)

Amounts of Milking from each cow were automatically recorded everyday by an auto milk recorder (manufactured by ORION MACHINERY CO., LTD.). Additionally, for each group of Section A and Section B, during the last 2 days in the ALA administration period of 14 days and the non-administration period of 14 days, 50 to 100 mL of milk was collected twice a day from cows of each period to use as milk samples for data analysis. The milk samples were preserved at −30° C. until the milk composition and the like were analyzed.

Using the above milk samples collected from each of the cows, the milk composition such as milk fat, proteins, casein, lactose, total solid (TS), solid not fat (SNF), milk urea nitrogen (MUN) and somatic cell count (SCC) was measured using a semi-solid infrared spectroscopy (Milko-Scan, 133N, manufactured by Foss Electric, Hill-erod (Denmark)). Data of each cow were calculated as an average value of 4 milk samples collected for 2 days. The results are shown in Table 3. For each group of Section A and Section B, the data average of the ALA administration periods (ALA Group A and ALA Group B) was shown under the item of ALA consumption groups, and the data average of the non-administration periods (Control Group A and Control Group B) was shown under the item of Control groups. The data were analyzed statistically as a crossover design using the mixing procedure of SPSS (PASW Statistics 18.0, manufactured by IBM). Statistical analysis of each result was carried out by mixed model and p<0.05(*) meant statistically significant difference. A tendency toward significance was considered at p<0.10.

TABLE 3

|  | Control groups | ALA consumption groups |
|---|---|---|
| Milk yield (Kg/day) | 23.95 ± 1.84 | 23.78 ± 1.67 |
| Milk composition (%) | | |
| Fat | 4.52 ± 0.23 | 4.42 ± 0.14 |
| Proteins | 3.47 ± 0.13 b | 3.51 ± 0.12 a |
| Lactose | 4.80 ± 0.03 | 4.82 ± 0.02 |
| Non-fat solid | 8.98 ± 0.15 | 9.03 ± 0.17 |
| Overall solid | 13.39 ± 0.36 | 13.34 ± 0.28 |
| Casein | 2.69 ± 0.09 b | 2.71 ± 0.09 a |
| MUN, mg/dl | 14.39 ± 2.26 | 14.87 ± 2.56 |
| Somatic cell count, ×10³ cells/mL | 7.59 ± 1.26 | 7.04 ± 0.62 |

Note that different letters (a, b) on the same row show significant difference (p <0.05). (±: standard error).

(Results)

As evident in Table 3, protein and casein contents increased significantly in the milk of lactating cows who consumed the feed to which 5-ALA was added (p<0.05). However, no particular differences were confirmed in milk yield, milk fat, lactose, non-fat solid, overall solid or MUN when compared with Control Groups. Additionally, no significant differences were confirmed in the values between Control Group A of Section A and Control Group B of Section B, thereby confirming that the impact of ALA administration is cleared by setting an adjustment period of 7 days even if an impact by microorganisms, protozoa, and the like on the rumen is considered.

The invention claimed is:

1. A method for increasing protein content proportion in milk of a lactating cow, comprising orally administering a compound shown by the following formula (I) or salt thereof to the lactating cow in an amount of 0.02 to 2 mg/kg of body weight/day in terms of 5- aminolevulinic acid,

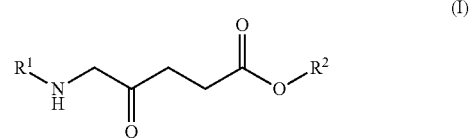

(I)

wherein R1 represents a hydrogen atom, a formyl group, an acetyl group, a propionyl group, or a butyryl group and wherein R2 represents a hydrogen atom, a methyl group, an ethyl group, a propyl group, a butyl group, or a pentyl group.

2. The method for increasing a protein content proportion in milk of a lactating cow according to claim 1, wherein the protein is casein.

* * * * *